(12) United States Patent
Ashford

(10) Patent No.: US 7,155,958 B2
(45) Date of Patent: Jan. 2, 2007

(54) HOLE DIAMETER MEASUREMENT

(75) Inventor: Curtis M. Ashford, St. Peters, MO (US)

(73) Assignee: The Boeing Company, Chicago, IL (US)

( * ) Notice: Subject to any disclaimer, the term of this patent is extended or adjusted under 35 U.S.C. 154(b) by 65 days.

(21) Appl. No.: 10/985,454

(22) Filed: Nov. 10, 2004

(65) Prior Publication Data

US 2006/0096351 A1    May 11, 2006

(51) Int. Cl.
*G01N 3/56* (2006.01)
(52) U.S. Cl. .............................................................. 73/7
(58) Field of Classification Search .................. 73/7, 73/866, 865.8, 865.9, 432.1; 33/545
See application file for complete search history.

(56) References Cited

U.S. PATENT DOCUMENTS

| | | | | |
|---|---|---|---|---|
| 1,396,117 | A * | 11/1921 | Iliff | 33/542 |
| 2,087,896 | A * | 7/1937 | Blomstrom | 33/543 |
| 2,456,497 | A * | 12/1948 | Forsmark | 33/542 |
| 2,472,139 | A * | 6/1949 | Emery et al. | 33/501.45 |
| 2,649,782 | A * | 8/1953 | Smith | 33/531 |
| 5,210,955 | A * | 5/1993 | Lewis | 33/558.01 |
| 2006/0081030 | A1* | 4/2006 | Kuhman et al. | 73/7 |

FOREIGN PATENT DOCUMENTS

| | | | |
|---|---|---|---|
| JP | 09133512 | A * | 5/1997 |

OTHER PUBLICATIONS

Chamfer & Countersink Gages Demystified; website article; Oct. 12, 2004; 4 pages; Brunswick Instrument, Inc., Niles, IL.
CrownLoc sales brochure; copyright 2002; 6 pages; Seco Carboloy, Global Metalworking Synergy.
Schuetz, George; Quality Gaging Tips, Gaging Countersunk and Chamfered Holes; online column; Oct. 8, 2004; 1 page; MMS Online; www.mmsonline.com/articles/0799/gage.html.
Precision Indicator Gage Ball System sell sheets; undated; 2 pages; Beamar Test & Measuring Systems.
Internet information regarding POP—Rivet Selection: Factors to Consider; 2 pages; www.emhart.com/products/pop/popex/factors.html.
Instruction Hardware Engineering; Jun. 14, 2004; 8 pages; L-3 Communications Corporation, Link Simulation & Training Division.
Salour; U.S. Patent Appl. No. 10/890,619; entitled Automated Drill Process for Two-Diameter Holes in Multi-Layer Variable Thickness Composite Materials; filed Jul. 14, 2004.

\* cited by examiner

*Primary Examiner*—Hezron Williams
*Assistant Examiner*—Tamiko Bellamy
(74) *Attorney, Agent, or Firm*—Harness Dickey & Pierce P.L.C.

(57) ABSTRACT

Methods of measuring the amount of wear at a hole. In a first embodiment, the method includes measuring a first diameter of the hole at a portion of the hole wall that is subject to wear and measuring a second diameter of the hole at a portion of the wall not subject to the wear. The measured diameters are then used to determine the amount of the wear. An assumption may be made regarding a profile of the wear. To determine the amount of the wear from the measured diameters, the Pythagorean Theorem may be used. Further, the method may include determining how far a fastener will protrude from the hole based on the amount of the wear. Moreover, the hole may be used to calibrate ring or chamfer gages.

16 Claims, 6 Drawing Sheets

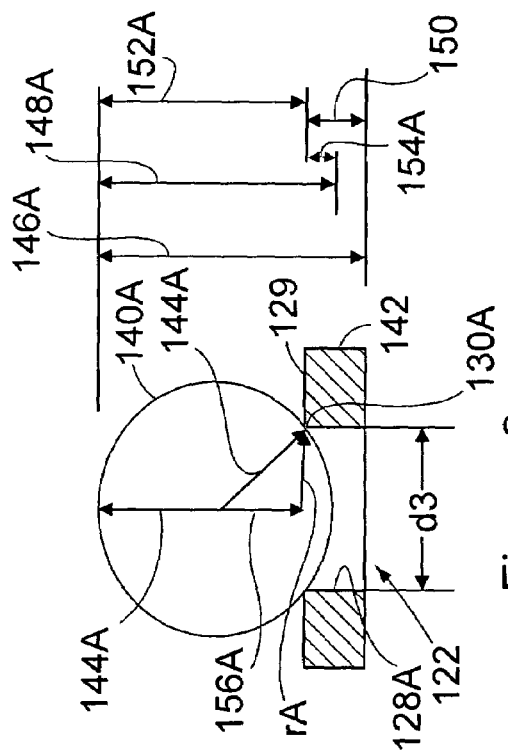
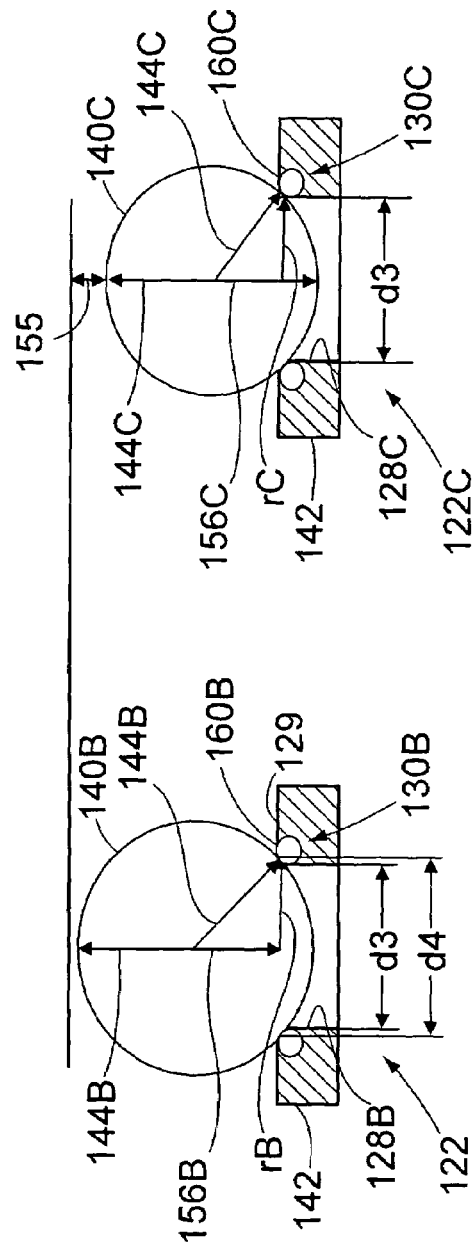

HOLE DIAMETER MEASUREMENT

FIELD OF THE INVENTION

This invention relates generally to metrology and, more particularly, to methods of determining the amount of wear occurring at the juncture of a hole surface and the top surface of a straight edged ring gage or a chamfered ring gage.

BACKGROUND OF THE INVENTION

Fasteners on commercial and military aircraft carry crucial loads from one component of the aircraft to the next. If the hole is too small for the fastener, the fastener may be difficult to install in the hole, may fit up improperly, or be preloaded in a non-optimal manner. These conditions can cause unwanted noise, create a joint that does not have optimal strength, and increase assembly cost of the aircraft. In addition, the head of the fastener might protrude from the surface of the joint farther than desired. At high aircraft speed, these improperly seated fastener heads would cause increased drag, which would cause additional fuel consumption, thereby necessitating the requirement for additional production steps to correct the condition.

Typically, fastener holes are created after the components to be joined are brought into their final assembly position and clamped together. A tool is then brought into contact with one of the components and advanced through both components to create the hole. The tool is then withdrawn thereby allowing the components to be unclamped for cleaning, chip removal, deburring, and other post-hole formation operations. It is usually desired for the holes to have a sharp edge at the surface of the components to allow the head of the fastener to seat against the component properly. Seated properly, the head of the fastener extends no more than a pre-determined height from the surface of the component.

Ideally, the components are brought back into their final assembly positions with little delay following the post-hole formation activities. The assemblers of the aircraft then measure the diameter of the hole, select an appropriately sized fastener, and fasten the components together. Frequently, though, delays are known to occur between hole formation and final fastener installation. During these delays additional operations may be performed on the components and in the vicinity of the fastener holes. These other operations subject the sharp edge of the hole to wear which causes the edge to become rounded. Additionally, errors and inaccuracies during the formation of the hole may also contribute to the rounding of the edge. It also sometimes occurs that the aircraft will be placed in service with removal of the fastener becoming necessary at some later time (e.g. for maintenance or repairs). If so, it is possible that conditions during the operation of the aircraft may cause additional wear to the hole edge. Also, the maintenance or repair activity may subject the edge of the hole to additional wear and rounding. Because of the rounding of the edge, the resulting measured hole diameter is usually larger than the true diameter of the hole (i.e. the diameter of the hole where the hole is not subject to the wear). The rounded shoulder is sometimes referred to as a "roll-off." By selecting a fastener in accordance with the diameter as measured at the roll-off, the problems associated with placing a fastener in an undersized hole are created.

A problem closely related to the installation of fasteners in undersized holes is the amount of wear that occurs on measurement standard ring gages used to calibrate "rivet gages." Rivet gages are rivets manufactured to exacting tolerances. These rivet gages are used to determine how far above the surface of a work piece the head of a rivet (of a pre-selected size) should protrude if inserted into a sharp edged hole of appropriate size. Because, the ring gages used to calibrate the rivet gages are subject to wear and rounding at the edges of the ring gage holes, a rivet gage inserted into a worn ring gage will protrude to a height less than it would in the absence of the wear. As a result, every rivet of the size calibrated with the ring gage will protrude above the work piece farther than expected.

Likewise, the accuracy of the calibration of chamfer gages can suffer from wear and roll off at the edge of the chamfered hole of the chamfer ring gage. The primary difference between calibrating chamfer gages and rivet gages is that the chamfer ring gage used to calibrate the chamfer gage includes a chamfered hole. Nonetheless, the intersection of the chamfered surface and the upper surface of the chamfer ring gage is rounded causing an apparent increase in the outer diameter of the chamfer. As a result, when the chamfer gage being calibrated is placed in the chamfer ring gage, the chamfer gage is set to indicate a larger diameter than it actually measures. As a result, chamfered holes measured with the improperly calibrated chamfer gage are smaller than the measured size indicates. Thus, the fasteners that ought to fit in the chamfer instead protrude from the surface farther than expected. The result is the same as with improperly calibrated rivet gages: increased production costs, increased fuel consumption and less than optimal fit up.

Thus, a need exists for a method of determining the amount of wear, or rounding, that occurs at the edge of a hole.

SUMMARY OF THE INVENTION

It is in view of the above problems that the present invention was developed. The invention provides methods for determining the amount of wear experienced at the edge of a hole.

In a first preferred embodiment, the method includes determining the amount of wear to a hole defined by a wall in a material. The wear generally occurs at the surface of the material and at portion of the wall of the hole that is adjacent to the surface. The method includes measuring a first diameter of the hole at a portion of the wall subject to the wear and measuring a second diameter of the hole at a portion of the wall spaced apart from the portion of the wall subject to the wear. From the measured diameters a determination is made of the amount of wear that has occurred at the hole. During the determination of the amount of wear an assumption may be made regarding a profile of the wear. Preferably, the assumed profile is a portion of a circle. Also, a sphere with a known diameter may be used to measure the diameter(s) of the hole. Further, it may be assumed that the sphere contacts the worn portion of the hole along a tangent common to the worn portion and the sphere. In a preferred embodiment, the Pythagorean Theorem is used to determine the amount of the wear.

In a second preferred embodiment, another method of measuring the amount of wear experienced by a hole in a material is provided. Of course, the material has a surface and a wall defining the hole. According to the current embodiment, the method includes measuring a first diameter of the wall at a first portion of the wall that is generally adjacent to the surface and subject to the wear. Also, the method includes measuring a second diameter of the wall at a second portion of the wall that is generally spaced apart from the surface. Using the measured diameters, the amount of the wear is determined. Preferably, the method includes using the hole to calibrate either a rivet gage or a chamfer gage. Moreover, the hole may be a chamfered hole. The method may also include determining a distance that a fastener of a pre-selected size will protrude above the surface of the material.

According to a third preferred embodiment, a method is provided for determining an amount of wear to a shoulder of a hole in a material. In the current embodiment, the hole is generally perpendicular to the surface of the material and the shoulder of the hole is adjacent to the surface. The method includes measuring a first diameter of the hole at the shoulder and measuring a second diameter of the hole at a location that is spaced apart from the shoulder. The amount of wear is then determined using the first measured diameter and the second measured diameter. Preferably, a third diameter of the hole can be measured at the shoulder to, for instance, verify conformity to the assumed profile and thus improve the accuracy of the method of the current embodiment.

In still another preferred embodiment, the present invention provides another method of determining the amount of wear to the edge of a hole. The method of the current embodiment includes selecting a member (e.g. a ring or chamfer gage) that defines a hole that, nominally, has a sharp edge at a surface of the member. A measurement is made of the diameter of the hole. Further, the member is subjected to wear that rounds the edge of the hole and the diameter is measured at the rounded edge. Using the two measurements of the diameter, the amount of wear is determined. Further, the member may be used to calibrate a rivet gage or a chamfer gage. Moreover, the rounding may be removed from the edge by, for example, lapping the surface of the member.

Further features and advantages of the present invention, as well as the structure and operation of various embodiments of the present invention, are described in detail below with reference to the accompanying drawings.

BRIEF DESCRIPTION OF THE DRAWINGS

The accompanying drawings, which are incorporated in and form a part of the specification, illustrate exemplary embodiments of the present invention and together with the description, serve to explain the principles of the invention. In the drawings:

FIG. 3 illustrates an apparatus for measuring the diameter of a fastener hole having a sharp edge;

FIG. 4 illustrates an apparatus of a preferred embodiment for measuring the diameter of a fastener hole with an edge that has been subjected to wear;

FIG. 5 illustrates another apparatus of the preferred embodiment of FIG. 4 for measuring the diameter of a fastener hole with an edge that has been subjected to wear;

DETAILED DESCRIPTION OF THE PREFERRED EMBODIMENTS

Figure 1:
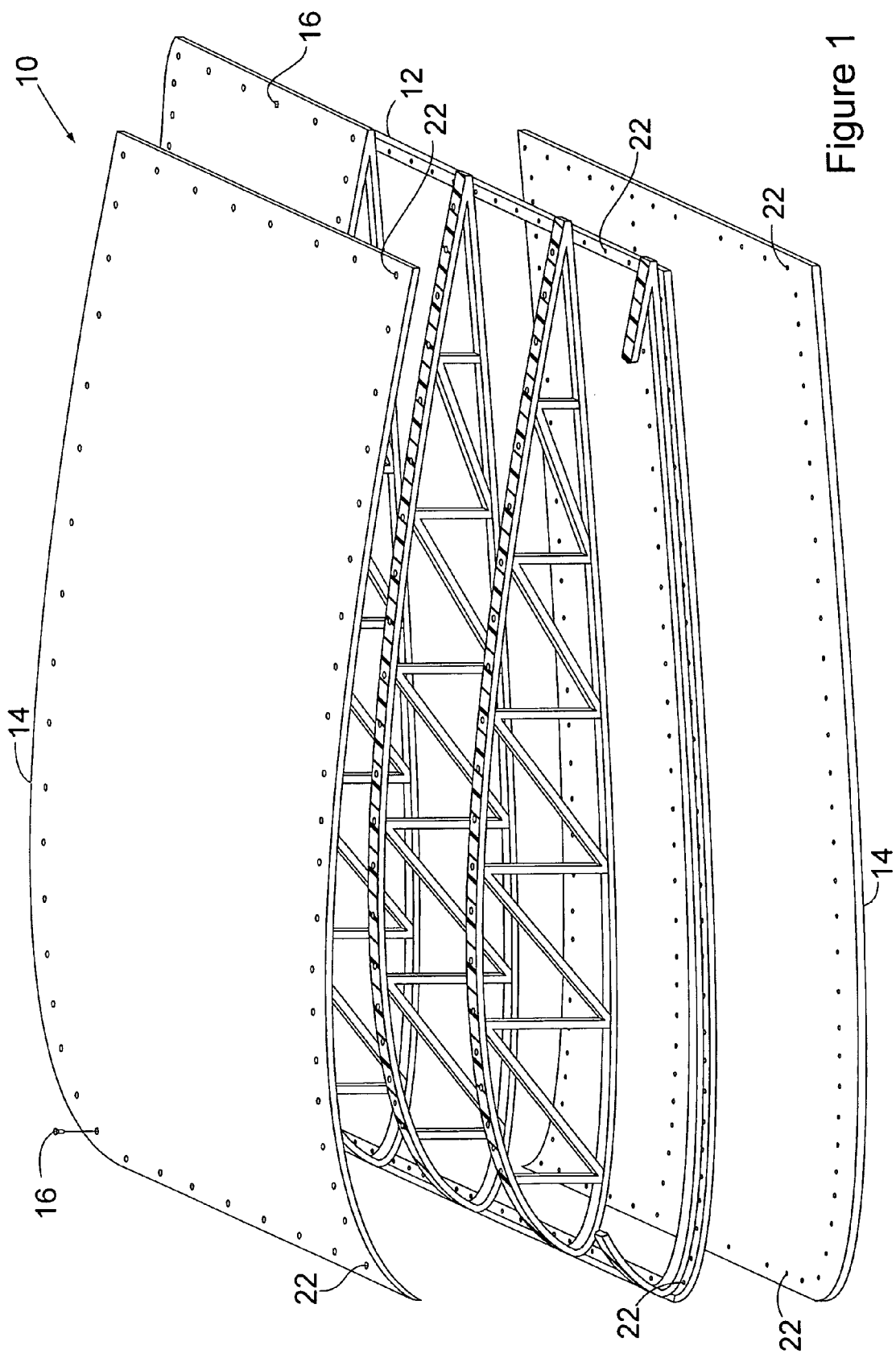
FIG. 1 illustrates an exploded view of a structure having fastener holes in accordance with the principles of the present invention.

Referring to the accompanying drawings in which like reference numbers indicate like elements, FIG. 1 illustrates an aircraft wing constructed in accordance with the principles of the present invention.

The wing of FIG. 1 includes a structure 12, several skin panels 14, numerous fasteners 16, and numerous fastener holes 22. The skin panels 14 fit over the structure 12 so that the corresponding fastener holes 22 align to allow the fasteners 16 to be installed in the holes 22. In the alternative, the holes 22 can be drilled with the panels 14 clamped in their final assembly locations on the structure 12. Techniques for in situ drilling are described in co-owned, co-pending, U.S. patent application Ser. No. 10/890,619, entitled Automated Drill Process for Two-Diameter Holes in Multi-Layer Variable Thickness Composite Materials, filed by Salour et al, on Jul. 14, 2004, which is incorporated herein as if set forth in full. The structure 12 carries the load of the aircraft which is supported by aerodynamic forces created on the panels 14 by air moving past the wing 10.

Figure 2:
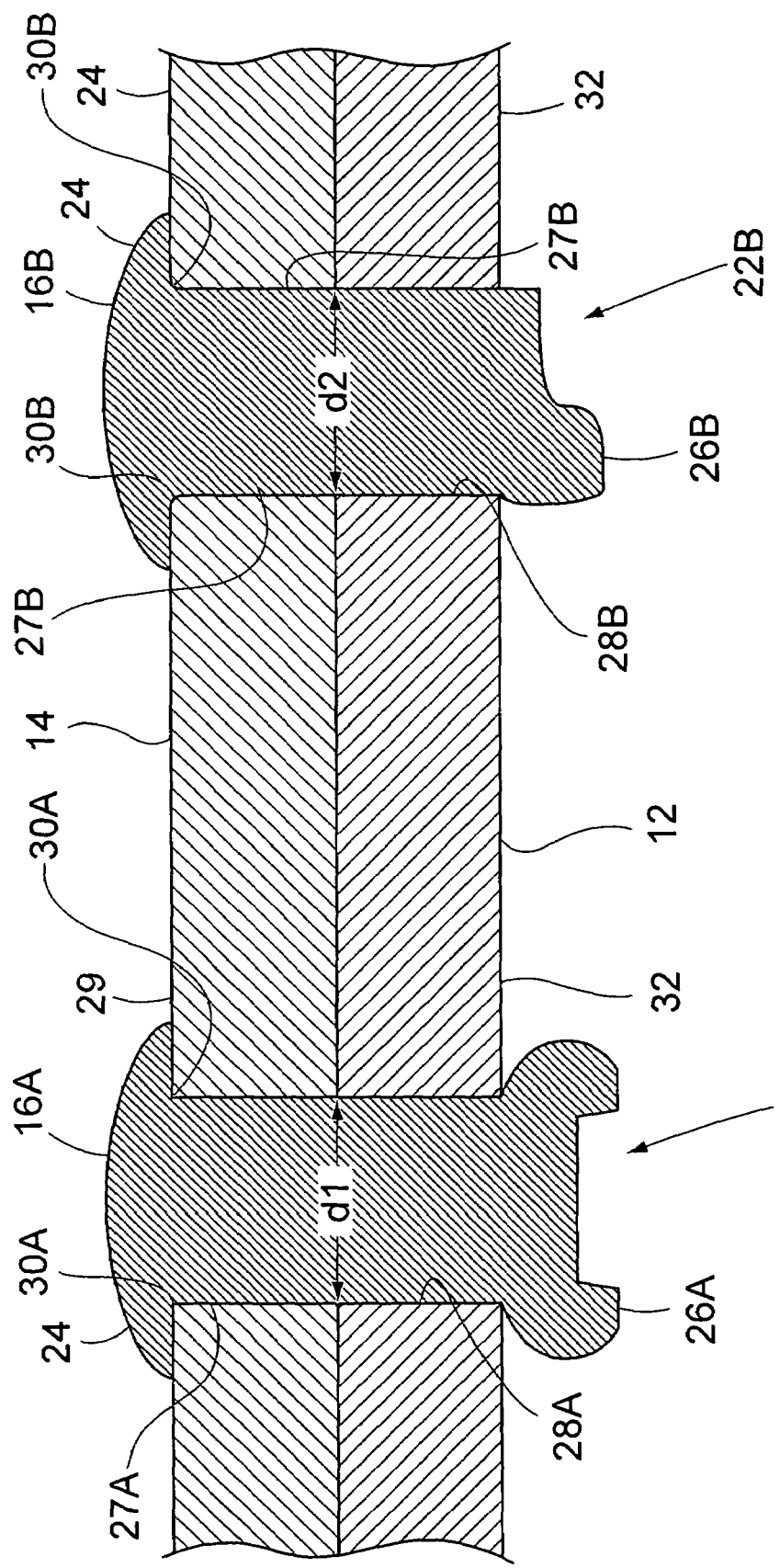
FIG. 2 illustrates a cross section of fasteners installed in fastener holes.

FIG. 2 illustrates the panel 14 fastened to the structure 12 with the fasteners 16 in the holes 22. FIG. 2 shows a manufactured head 24 of each of the fasteners 16, an upset head 26, a grip or shank 27, a wall 28 of the hole 22, an outer surface 29 of the panel 14, an edge 30 of the hole 22, and an inner surface 32 of the structure 12. As shown, the fasteners 16 are preferably rivets because of their relative versatility in joining components of different materials and their ease and low cost of installation. Nominally, after the diameter "d" of the hole 16 is measured, the size of the rivet 16 is selected so that the grip 27 will substantially fill the hole 16 when inserted in the hole. When the rivets 16 are inserted in the hole 22, the manufactured head 24 of each of the rivets nominally rests flush against the outer surface 29 of the panel 14. The rivet 16 is then popped into place whereby the upset head 26 is formed.

On occasion the measured diameter of the hole 16 will be larger than the actual diameter because of the wear or rounding of the edge 30. In FIG. 2, the diameter "d1" was measured with sufficient accuracy that the proper size was selected for the rivet 16A. In contrast, an inaccuracy occurred in the measurement of the diameter "d2" of hole 22B that resulted in a slightly over-sized rivet 16B being selected for hole 22B. Because the grip of the rivet 16 is too large for the diameter "d2" of the hole 16B, the upset head 26B of the rivet 16B did not form properly. Instead of having the crown shaped upset head 26A of the rivet 16A, the rivet 16B has an irregularly shaped upset head 26B that might not even hold the rivet 16B in the hole 22B. Accordingly, extra effort will be expended to install another rivet 16B in the hole 22B. Since the selection of the rivet 16 will still likely depend on the inaccurate measurement of the diameter "d2" it is possible that several repetitions of the riveting procedure will occur before an optimal joint between the panel 14 and the structure 12 will be created. To solve these problems, and others, the present invention provides methods and apparatus to ensure that hole diameters are accurately measured. While the current embodiment depicts a riveted wing 10, any fastened assembly can be constructed in accordance with the principles of the present invention.

Turning now to FIG. 3, an apparatus used to measure the diameter "d3" of a hole 122 in a ring gage 142 is shown. In the current embodiment, a sphere 140A is placed over the hole 122 to calibrate the gage 142 (i.e. to measure the diameter of the hole 122 that is defined by the ring gage 142). The sphere 140A has a known diameter 148A that is larger than the diameter "d3" so that, when placed over the hole 122, the sphere 140A protrudes above the surface 129 by some height 152A. The diameter 148A (and radius 144A) of the sphere 140A is known with great accuracy and is usually maintained to within as little as 0.00001" of the known value. It is thus possible to determine the hole diameter "d3" from the height of the sphere protrusion 152A.

More particularly, FIG. 3 shows a sphere radius 144A, an overall height 146A, the sphere diameter 148A, a reference surface height 150, the sphere protrusion height 152A, a depth or distance 154A, and an adjusted height 156A. The overall height 146A can be measured directly using, for example, a calibrated dial gage. Since the radius 144A is known because it is one half of the known sphere diameter 148A, the remaining distances can be easily derived. Specifically, the sphere protrusion 152A above the ring gage 142 is the difference between the overall height 146A and the height 150 of the ring gage 142 (that can also be measured directly). The depth 154A that the sphere 140A protrudes into the hole 122A is the difference between the sphere diameter 148A and the sphere protrusion 152A. Also, the adjusted height or distance 156A from the center of the sphere 140A to the top surface 129 of the ring gage 142 is the difference between the radius 144A and the depth 154A that the sphere protrudes into the hole 122.

In operation, a user who wishes to measure the diameter "d3" of the hole 122 places the sphere 140A over the hole 122. From the measured sphere protrusion 152A it is possible to calculate the radius d3 with simple trigonometric equations (assuming that the hole has a sharp or square edge 130A). In the alternative, for each sphere 140A of a given radius 144A a chart may be developed that correlates the protrusion 152A and the diameter d3. The latter approach is frequently preferred in a shop environment.

In practice, though, the edge of the hole 130A is subject to wear and does not remain sharp. Rather, the edge 130A eventually becomes worn, or rounded, and becomes more of a shoulder than an edge. Such a condition is reflected in FIG. 4 where the edge 130B has become rounded. The rounding is shown by the arc of the circle 160B at the intersection of the surface 129 and the wall 128B. The shoulder 130B allows the sphere 140B to settle in the hole 122B at a depth 154B that is slightly greater than the depth 154A of FIG. 3. Importantly, the diameter "d4" of the hole 122B is measured across the shoulder 130B (at the arc of the circle 160B). Since material has been worn away from the shoulder 130B, the measured diameter "d4" is larger than the true diameter "d3."

Also, if the ring gage 142 is used to calibrate a rivet gage, the rivet gage will be seated in the hole 122 at a depth greater than it would have been seated had the wear not occurred at the shoulder 130B. As a result, the protrusion of the rivet gage above the surface 129 will be less than the protrusion of the rivet gage in a hole 122 not subject to the wear (i.e. having a sharp edge 130A). Thus, rivets of the same size as the rivet gage will protrude further than expected from the surface of a work piece in which they are installed.

Figure 6:
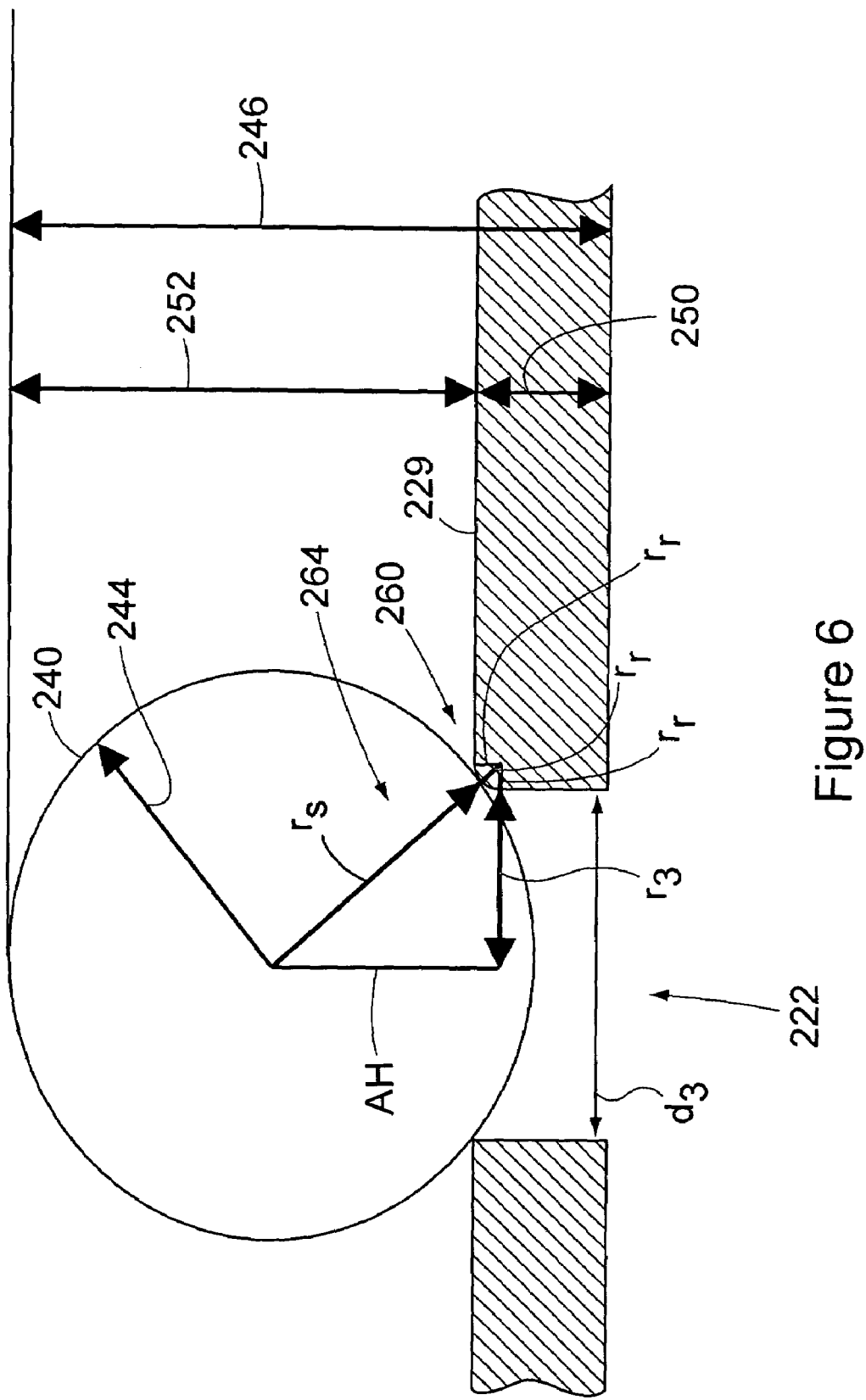
FIG. 6 further illustrates the apparatuses of FIGS. 4 and 5.

With reference now to FIG. 6, the mathematic basis of a preferred method of determining the true bore "d3" of the hole 222 is shown. FIG. 6 differs from FIG. 4 generally by showing a radius of the hole "r3," a radius of the roll-off (or shoulder) "rr," a sphere radius "rs," and a triangle 264 that defines a relationship between these distances "r3," "rr," "AH" and "rs." It is assumed that the roll-off 260 is generally circular although other profiles (e.g. linear or exponential) could be assumed for the roll-off 260. In FIG. 6, the triangle 264 is a right triangle with one vertex at the center of the sphere 240, another vertex at the center of the roll-off 260, and the third vertex on the centerline of the hole 222 at a height defined by the center of the roll-off 260. The assumption of the circular profile for the shoulder 260 means, among other things, that the sphere 240 and the shoulder 260 will meet along a common tangent line with their centers separated by a distance equal to the sum of the radii of the circles 240 and 260 (i.e., "rr" and "rs").

The sides of the triangle 264 follow the Pythagorean theorem from which the roll-off radius "rr" can be determined. More particularly the length of the hypotenuse of the triangle 264 is defined by the sum of the sphere radius 244 (hereinafter "rs") and the roll off radius "rr." The second side of the triangle 264 (that extends downwardly from the center of the sphere 240) has a length or adjusted height "AH" equal to the overall height 246, minus the sphere radius "rs" and the height 250 of the ring gage (work piece), plus the roll off radius "rr." The third side of the triangle 264 has a length equal to the bore radius "r3" plus the roll-off radius "rr." Each of these sides therefore has a length equal to the roll-off radius "rr" plus a known, or easily derived, value. Using the Pythagorean Theorem and reducing the resulting equation yields the following equation:

$$rr^2+2*rr*(AH+r3-rs)+AH^2+r3^2-rs^2=0$$

Since the bore radius r3 was previously measured (e.g. when the hole was initially formed) and the adjusted height "AH" and the radius of the sphere "rs" are known, the equation has one unknown the roll-off radius "rr." Further, the equation is a quadratic equation that can be solved directly to yield the unknown "rr." In another preferred embodiment, a "what-if" analysis is run that drives the left side of the equation to zero to determine the value of the roll-off radius "rr". One important advantage of knowing the roll-off radius "rr" includes being able to set limits on the amount of wear experienced by a ring gage 142. If the wear (i.e. the roll-off radius "rr") becomes excessive, a different ring gage may be placed in service. In the alternative, the edge 130 can be restored to a sharp, or square, condition by lapping the surface 129 to remove material from the surface of the ring gage 142 down to a depth at least equal to the roll-off radius "rr."

As noted previously, the profile of the wear (e.g. the shape of the shoulder 160B) was assumed to be circular. Since the profile might have a different profile, the present invention also includes a method to improve the accuracy of determining the amount of wear at the shoulder 160B of the hole 122. More particularly, as shown in FIG. 5, a second sphere 140C having a different diameter than the diameter of the sphere 140B (see FIG. 4) may be used to determine the roll-off radius "rr." The difference in sphere radii 144B and 144C causes the sphere 140C to contact the shoulder 130C at a different location and to protrude from the hole 122 by a different height than the sphere 140B. The difference in these heights is illustrated at reference 155 in FIG. 5. Again, the various heights of concern can be measured or derived to reach a second determination of the roll-off radius "rr." With the roll-off radius "rr" determined and, if desired, the ring gage 142 machined to remove the rounding of the edge 130B, the ring gage 142 may thus be used to calibrate rivet gages.

Figure 7:
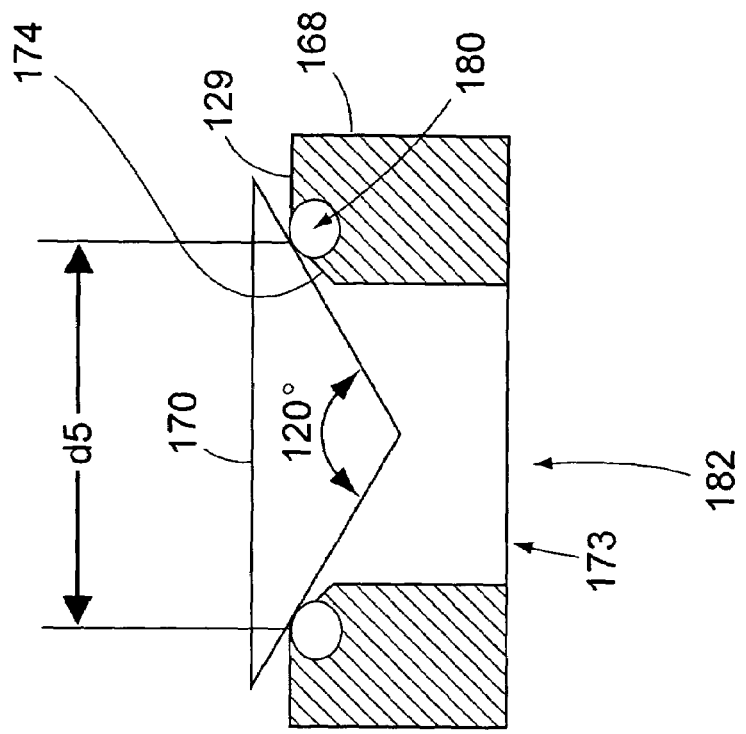
FIG. 7 illustrates an apparatus in accordance with another preferred embodiment for calibrating a chamfer gage.
Figure 8:
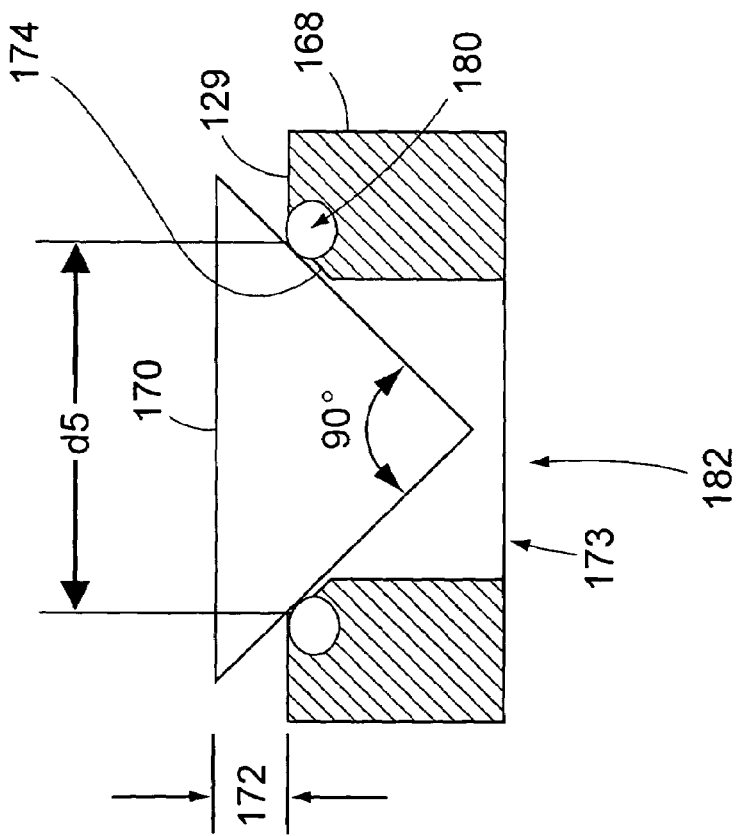
FIG. 8 illustrates the apparatus of FIG. 7 being used to calibrate another chamfer gage.

In an alternate embodiment, a chamfer ring gage 168 may be used to calibrate chamfer gages 170 as shown by FIGS. 7 and 8. The ring gage 168 shown includes a chamfered surface 174 at the end of the hole adjacent the surface 129. During the calibration of the chamfer gage 170, the chamfer gage 170 is placed in the hole 173 and the protrusion 172 of the chamfer gage 170 above the surface 129 is measured. From the measured protrusion 172, a determination is then made (by, for instance, reference to a look up table) of the outer chamfer diameter "d5" of the hole 173. Even though the chamfer 174 and the hole 173 of the ring gage 168 are initially formed with a high degree of accuracy, the chamfer ring gage 168 may also experience wear. In particular, as the chamfer ring gage 168 is used to measure various articles, an edge 180 (formed where the chamfer 174 and the surface 129 meet) becomes worn or rounded. Like the rounding of the edges 130A–C (FIGS. 3 to 5) and edge 260 (FIG. 6), the rounding of the edge 180 causes inaccuracy in the calibration of the chamfer gage 170. More particularly, the roll-off 180 causes the angled side 182 of the chamfer gage 170 to contact the chamfer ring gage 168 at a point where the measured diameter is greater than the outer chamfer diameter "d4" of a ring gage 168 without wear. Accordingly, the measured outer diameter of the chamfer 174 is greater than the initial outer chamfer diameter. Thus, the calibration of the chamfer gage 170 includes an inaccuracy due to the wear experienced by the chamfer ring 168.

Fortunately, the roll-off radius "rr" of the shoulder 180 can also be characterized in accordance with the present invention. If the wear experienced by the chamfer ring 168 becomes excessive the chamfer ring 168 can be replaced with an un-worn chamfer ring 168. Thus, the chamfer gages 170 that are calibrated in accordance with the principles of the present invention possess greater accuracy than chamfer gages 170 calibrated per previously available methods.

Figure 9:
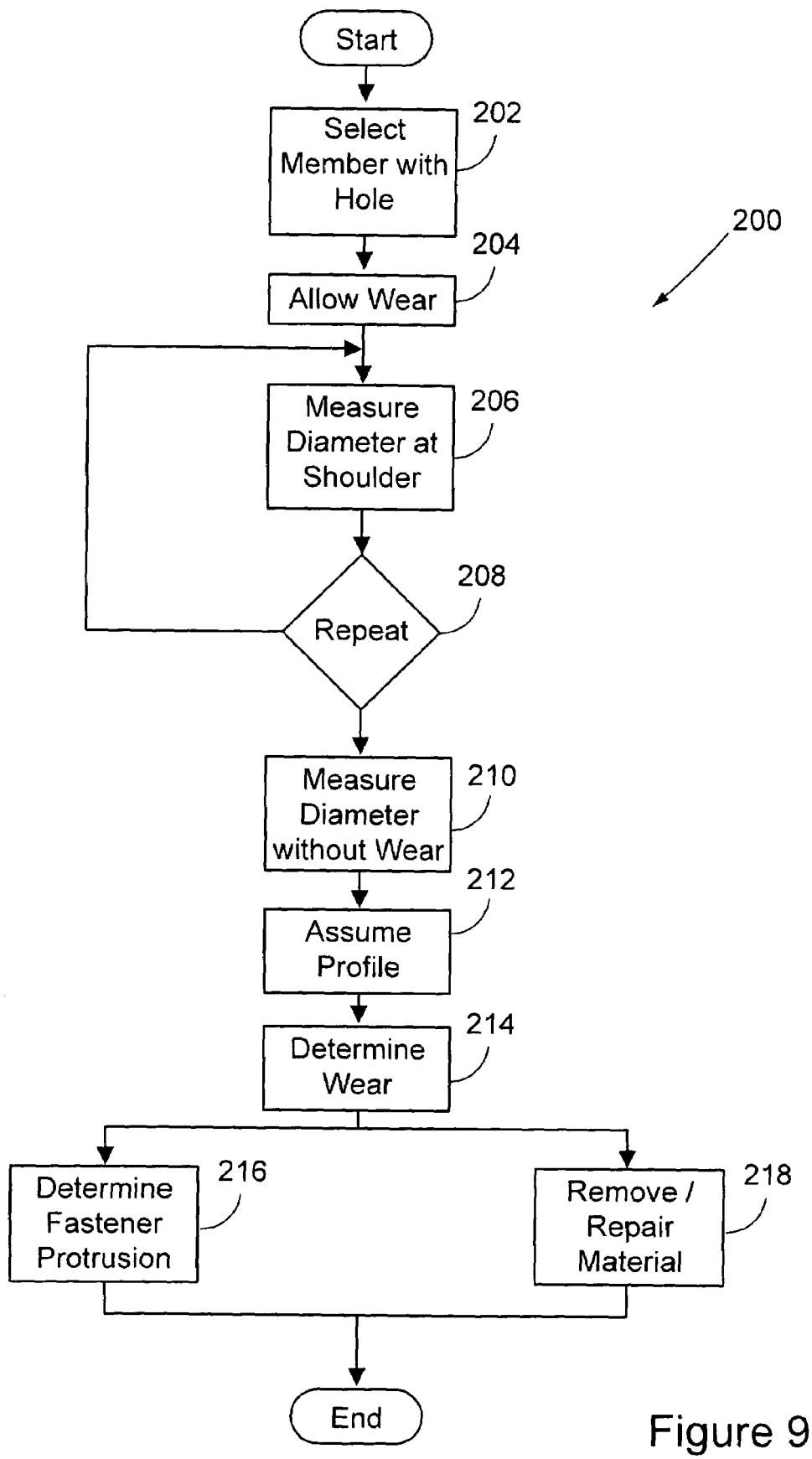
FIG. 9 illustrates a method in accordance with the principles of the present embodiment.

With reference to FIG. 9, a method in accordance with the principles of the present invention is illustrated. The method 200 generally includes measuring the diameter of a hole at a shoulder of the hole, measuring the true diameter of the hole, and determining the amount of wear that the shoulder has experienced. More particularly, FIG. 9 shows a member that defines a hole being selected, designed, or manufactured in operation 202. The member is then subjected to wear that affects the shoulder of the hole as in operation 204. At a time selected by the user, the diameter of the hole is measured at the shoulder. See operation 206. If it is desired, the diameter of the hole may be measured again as indicated by the decision illustrated at operation 208. Operation 210 illustrates that at some time (e.g. when the hole is initially formed) the hole diameter is measured. An assumption is also made as to the profile of the shoulder. See operation 212. Using the assumption and the measurements of the hole diameter, a determination is made of the amount of wear present at the shoulder as illustrated by operation 214. Further, the wear may be used in determining how far a fastener will protrude from a fastener hole as in operation 216. In the alternative, the wear may be removed or repaired as in operation 218.

The embodiments were chosen and described in order to best explain the principles of the invention and its practical application to thereby enable others skilled in the art to best utilize the invention in various embodiments and with various modifications as are suited to the particular use contemplated.

As various modifications could be made in the constructions and methods herein described and illustrated without departing from the scope of the invention, it is intended that all matter contained in the foregoing description or shown in the accompanying drawings shall be interpreted as illustrative rather than limiting. Thus, the breadth and scope of the present invention should not be limited by any of the above-described exemplary embodiments, but should be defined only in accordance with the following claims appended hereto and their equivalents.

What is claimed is:

1. A method of determining the amount of wear to a hole defined by a wall in a material, the method comprising:
    measuring a first diameter of the hole at a first portion of the wall subject to the wear, the wear generally occurring on a surface of the material and the first portion of the wall subject to the wear;
    measuring a second diameter of the hole at a second portion of the wall spaced apart from the first portion of the wall subject to the wear; and
    further comprising using a sphere with a known diameter to measure the first diameter in determining the amount of the wear.

2. The method according to claim 1, further comprising assuming that the wear of the wall has a profile that is a portion of a circle.

3. The method according to claim 1, further comprising assuming the sphere contacts the portion of the wall subject to wear tangentially.

4. A method of determining the amount of wear to a hole defined by a wall in a material, the method comprising:
    measuring a first diameter of the hole at a first portion of the wall subject to the wear, the wear generally occurring on a surface of the material and the first portion of the wall subject to the wear;
    measuring a second diameter of the hole at a second portion of the wall spaced apart from the first portion of the wall subject to the wear; and
    further comprising using the Pythagorean theorem in the determining the amount of the wear.

5. A method of measuring an amount of wear experienced by a hole in a material, the material having a surface and a wall defining the hole, the method comprising:
    measuring a first diameter of the wall at a first portion of the wall generally adjacent to the surface and being subject to the wear;
    measuring a second diameter of the wall at a second portion of the wall generally spaced apart from the surface; and
    further comprising determining a distance that a fastener of a pre-selected size will protrude above the surface of the material based on the amount of wear in determining the amount of the wear.

6. The method according to claim 5, further comprising assuming a profile of the wear.

7. The method according to claim 6, further comprising the assumed profile being a portion of a circle.

8. The method according to claim 5, further comprising using the hole to calibrate at least one of a rivet gage or a chamfer gage.

9. The method according to claim 5, wherein the hole is a chamfered hole.

10. A method of determining an amount of wear to a shoulder of a hole in a material, the hole being generally perpendicular to a surface of the material and the shoulder being adjacent to the surface, the method comprising:
    measuring a first diameter of the hole at the shoulder;
    measuring a second diameter of the hole at a location in the hole that is spaced apart from the shoulder; and determining the amount of wear using the first measured diameter and the second measured diameter; wherein the step of measuring the first diameter further comprises inserting a standard with a known dimension into the hole adjacent the shoulder to engage the shoulder, measuring an amount that the standard protrudes from the hole when engaged with the shoulder; and executing a prescribed geometric algorithm with reference to the standard's known dimension and the amount of the standard's protrusion to generate the measurement of the first diameter.

11. The method according to claim 10 further comprising measuring a third diameter of the hole at the shoulder and using the third measured diameter in the determining the amount of the wear.

12. A method of determining an amount of wear to the edge of a hole, comprising:
selecting a member that defines a hole, the hole to have a sharp edge at a surface of the member;
measuring a first diameter of the hole;
allowing the member to be subject to wear that rounds the edge;
measuring a second diameter of the hole at the rounded edge;
determining the amount of wear using the first and second measurements; wherein the step of measuring the first diameter further comprises inserting a standard with a known dimension into the hole adjacent the shoulder to engage the shoulder, measuring an amount that the standard protrudes from the hole when engaged with the shoulder; and executing a prescribed geometric algorithm with reference to the standard's known dimension and the amount of the standard's protrusion to generate the measurement of the first diameter.

13. The method according to claim 12, wherein the member is a ring gage.

14. The method according to claim 13, further comprising using the ring gage to calibrate a rivet gage.

15. The method according to claim 13, further comprising using the ring gage to calibrate a chamfer gage.

16. The method according to claim 12 further comprising removing the rounding from the edge.

* * * * *